United States Patent [19]
Bräutigam et al.

[11] Patent Number: 5,904,919
[45] Date of Patent: May 18, 1999

[54] COMPOSITION FOR PERMANENT WAVING OF HUMAN HAIR

[75] Inventors: Ina Bräutigam, Darmstadt; Bernd Nöcker, Ober-Ramstadt; Burkhard Rose, Darmstadt; Jörg Schneider, Griesheim, all of Germany

[73] Assignee: Goldwell GmbH, Germany

[21] Appl. No.: 08/897,286

[22] Filed: Jul. 21, 1997

[30] Foreign Application Priority Data

Jul. 26, 1996 [DE] Germany ............ 196 30 262.5

[51] Int. Cl.$^6$ ............... A61K 7/06; A61K 7/07
[52] U.S. Cl. ............... 424/70.2; 424/70.5; 424/70.51; 424/70.122
[58] Field of Search ............ 424/70.2, 70.5, 424/70.51, 70.122

[56] References Cited

U.S. PATENT DOCUMENTS

| | | | |
|---|---|---|---|
| 5,472,689 | 12/1995 | Ito | 424/70.122 |
| 5,618,525 | 4/1997 | Bunning | 424/70.122 |
| 5,690,129 | 11/1997 | Bunning | 132/200 |
| 5,747,016 | 5/1998 | Yui | 424/401 |
| 5,756,080 | 5/1998 | Janchitraponvej | 424/70.122 |

FOREIGN PATENT DOCUMENTS

| | | |
|---|---|---|
| 0640643 | 3/1995 | European Pat. Off. . |
| 2912484 | 10/1980 | Germany . |
| 4443062 | 6/1996 | Germany . |

*Primary Examiner*—Sally Gardner-Lane
*Attorney, Agent, or Firm*—Londa and Traub LLP

[57] ABSTRACT

A permanent waving composition showing excellent waving properties and, at the same time, a hair conditioning effect contains a) at least one reducing organic thio compound and (or) an inorganic sulfite; and b) at least one organopolysiloxane, whereby at least one silicium atom is linked to an alkylene group containing a hetero atom, particularly a nitrogen atom, together with a poly-(N-acyl alkylene imine) with units of the formula

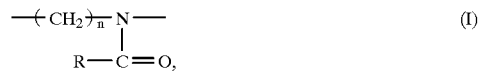

wherein n is a number from 1 to 5 and R is hydrogen, a $C_1$–$C_{12}$-alkyl, cycloalkyl, aralkyl or aryl group.

8 Claims, No Drawings

COMPOSITION FOR PERMANENT WAVING OF HUMAN HAIR

BACKGROUND OF THE INVENTION

This invention refers to a composition for waving of human hair, i.e. a permanent waving composition, providing an excellent waving effect, particularly leading to a uniform permanent wave with elastic curls and good combability, avoiding damage of the hair texture, also when applied repeatedly, but rather causing a conditioning effect and producing expressive lustre on the hair.

It is well-known that permanent waving is performed in a two-step process, i.e., reductive splitting of cystine disulfide bonds of the hair by the action of a reducing agent and subsequent neutralization or fixing of the wave by the application of an oxidizing agent whereby the cystine disulfide bonds are restored.

The reducing agent most commonly used is still thioglycolic acid, particularly the ammonium salt, although numerous other thio compounds have been suggested for this purpose which, however, have not been generally accepted in practical use.

The compositions comprising thioglycollate are normally used at a pH-value between 8 and 10, particularly from 8.5 to 9.5, which may cause hair damage when repeatedly applied within short intervals.

There have been attempts to circumvent these disadvantages by the creation of so-called "acidic permanent waving solutions" with a pH-value in the range from 6.8 to 7.8, i.e. near neutral. The reducing agent most frequently employed for this purpose is thioglycolic acid monoglycerol ester. However, this material has proved to have a skin irritating and sensitizing potential on some users, so that this solution of the problem is not optimal either.

SUMMARY OF THE INVENTION

It has now been found that these disadvantages can be overcome by the creation of a permanent waving composition based on at least one reducing organic thio compound and (or) an inorganic sulfite, performing a homogeneous waving effect without damaging the hair texture in any way, and yet providing luster and good combability on the hair. Such a composition is prepared by the addition of at least one organopolysiloxane which has at least one silicium atom linked with an alkylene group containing a hetero atom, particularly nitrogen, bonded with a poly-(N-acyl alkylene imine) with groups of the formula I

(I)

wherein n is a number from 1 to 5 and R is hydrogen, a $C_1-C_{12}$-alkyl or cycloalkyl, aralkyl or aryl group, preferably in a proportion of 0.01% to 5% by wt., particularly 0.05% to 1% by wt., calculated to the total composition.

DETAILED DESCRIPTION OF THE INVENTION

Preferred organopolysiloxane polymers are published in European Patent Application No. 640,643, particularly, optionally quaternized aminoalkyl, preferably aminopropyl dimethyl polysiloxane/polyethyloxazoline copolymers of the formula

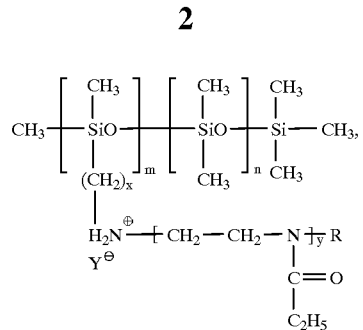

wherein m and n represent whole numbers from 20 to 10,000 each, particularly from 50 to 7000, optimally from 100 to 5000, x stands for a number from 1 to 5, preferably 3, and y is a number from 5 to 30, R denotes a $C_1-C_{12}$-alkyl or aryl group, particularly a methyl, ethyl or benzyl group, and $Y^-$ is an anion.

The preparation of the aminoalkyl dimethyl polysiloxane/polyethyloxazoline grafted copolymers preferably used according to the invention is described in detail in European Patent Application No. 640,643 mentioned above and is performed in accordance with the following structure scheme:

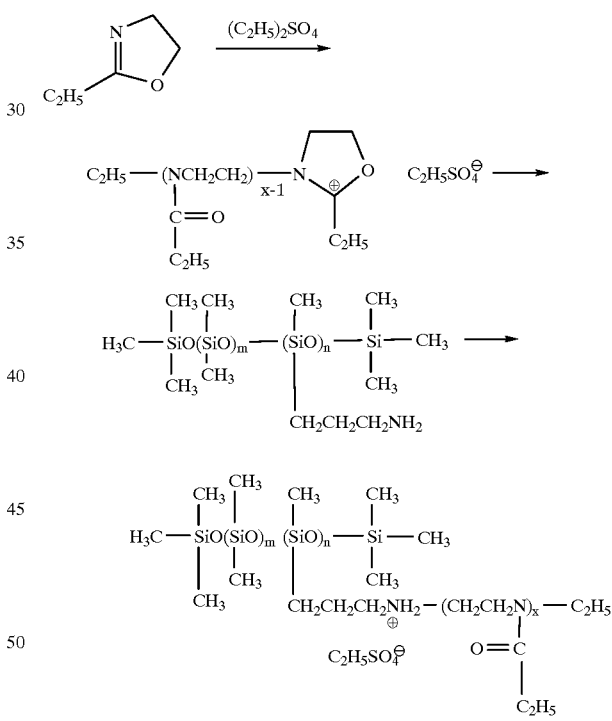

Anion $Y^-$ of the general formula may of course be different from the ethyl sulfate anion of the above example, i.e. the quaternization may also be performed with methyl chloride, dimethyl sulfate, benzyl chloride, dodecyl bromide, etc.

A particularly preferred grafted copolymer of the type illustrated above has a total molecular weight about from 50,000 to about 500,000, preferably about from 80,000 to about 300,000, particularly about 100,000 Dalton, whereby the molecular weight of the oxazoline section is from about 2,500 to about 7,500, preferably from about 4,000 to about 6,000, especially about 5,000 Dalton per section, i.e., the molecular ratio is about 20 units per molecule. Accordingly, the preferred Si-contents is about 50%.

Especially useful are the organopolysiloxanes described in European Patent Application No. 640,643 as No. A-1, A-2 and A-3 on pp. 12 to 13. The proportion of the grafted copolymers in the hair compositions according to the invention is from about 0.05% to 5%, preferably from 0.1% to 2.5%, particularly from 0.5% to 1.5% by wt. of the total composition.

The permanent waving compositions according to the invention comprise at least one reducing organic thio compound and (or) an inorganic sulfite. Preferred materials are thioglycolic acid and thiolactic acid and their salts, particularly the ammonium and ethanolamine salts.

Other suitable thio compounds are primarily cysteine or its hydrochloride, homocysteine, cysteamine, N-acetyl cysteine, thioglycerol, ethanediol monothioglycollate, 1,2-propylene glycol monothioglycollate (cf. WO-A 93/1791), 1,3-propanediol monothioglycollate or the isomer mixture resulting therefrom, 1,3-butanediol and 1,4-butanediol monothioglycollate or their isomer mixtures, ethanediol monothiolactate, 1,2-propanediol and 1,3-propanediol monothiolactate and their isomer mixtures, 1,3-butanediol and 1,4-butanediol monothiolactate and their isomer mixtures, polyethylene glycols such as di-, tri- and tetraethylene glycol monothioglycollates and monothiolactates, polypropylene glycols such as di-, tri-, and tetrapropylene glycol monothiolactates and monothioglycollates, glycerol monothiolactate and further thio acids and esters as well as mixtures thereof.

The total reducing agent contents in the compositions according to the invention is normally from 2.5% to about 15% by wt., calculated to free thioglycolic acid as reference substance.

Useful inorganic sulfites are especially alkali sulfites and hydrogen sulfites.

If necessary, the reducing permanent waving compositions may contain alkalizing agents. The quantity depends on the type of active reducing agent and the attempted pH-value of the composition. Preferably the reducing agent composition contains from about 0.1% to about 5%, particularly from about 0.5% to about 2.5%, by wt. of the alkalizing compound.

Preferred alkalizing agents within the scope of the invention are ammonium carbamate, ammonia and (or) ammonium (bi)carbonate. The preferred pH-value is in the range from about 6.5 to about 9.5, preferably from 7 to 8.5.

The permanent waving compositions used according to the invention may preferably also contain surfactants. Their proportion is from about 0.1% to about 10%, particularly from about 1% to about 5% by wt., of the reducing composition.

The surfactants used in both, reducing compositions and neutralizing compositions, are preferably of the anionic type, which may optionally be used in combination with nonionic surfactants.

Suitable anionic surfactants are preferably the well-known alkyl ether sulfates and carboxylic acids, particularly in the form of their alkali salts, and protein fatty acid condensates.

Suitable nonionic surfactants are preferably $C_8$–$C_{18}$-fatty alcohol polyglycol ether, fatty acid polyglycol ester, fatty acid alkanolamides, amine oxides and optimally $C_8$–$C_{18}$-alkyl polyglucosides.

Amphoteric surfactants may also be used such as the known betaines and amidobetaines and, particularly in cationic neutralizing compositions, cationic surfactants such as quaternary ammonium compounds.

Another desirable compound used in the reducing agent compositions according to the invention is $C_3$–$C_6$-alkanediol or its ether, particularly mono-$C_1$–$C_3$-alkyl ether.

Preferred compounds for this purpose are 1,2- and 1,3-propanediol, 1-methoxypropanol(-2), 1-ethoxypropanol(2), 1,3- and 1,4-butanediol, diethylene glycol and its monomethyl and monoethyl ethers as well as dipropylene glycol and its monomethyl and monoethyl ethers.

The proportion of these diols is preferably from 0.5% to 30%, particularly from about 1% to about 15%, especially from about 5% to about 10% by wt. of the reducing composition.

In addition to $C_3$–$C_6$-alkanediols or their ethers, other monoalcohols such as ethanol, propanol-1, propanol-2 and polyalcohols such as glycerol and hexanetriol, ethyl carbitol, benzyl alcohol, benzyloxyethanol and propylene carboxylate (4-methyl-1,3-dioxolane-2-one), N-alkyl pyrrolidone and urea may be used.

Particularly preferred additional ingredients are anionic, cationic, nonionic and amphoteric polymers, especially cationic polymers, preferably in a proportion from about 0.25% to about 5%, particularly from about 0.5% to 2.5% by wt. of the total waving composition.

Suitable polymers are particularly those of the type "Polyquaternium" according to "CTFA International Cosmetic Ingredient Dictionary", 4th Ed.

The compositions used according to the invention may of course contain all compounds generally used in permanent waving compositions which are not detailed here. They may be formulated as (aqueous) solutions, emulsions, creams, foams, etc.

To avoid repetition, reference is made to the state of the art, e.g., as described in "Ullmann's Encyclopedia of Industrial Chemistry", Vol. A12 (1986), pp. 588 to 591 and, in particular, the monography of K. Schrader, "Grundlagen und Rezepturen der Kosmetika", 2nd Ed. (1989, Hüthig Verlag, Heidelberg), pp. 823 to 840, and the survey of D. Hollenberg et al. in "Seifen-Öle-Fette-Wachse" 117 (1991), pp. 81 to 87.

The compositions and individual ingredients disclosed therein, which are included by reference, may also be used within the scope of this invention.

Optionally, a pre-treatment may be applied before the application of the reducing composition, e.g., as described in German Patent Application No. 37 40 926. After the application of this pre-treatment, the hair is wound on curlers and then the reducing composition is applied. After a processing time of about 15 to 30 minutes and rinsing, the hair is neutralized with a peroxide or bromate composition well-known by the state of the art.

Likewise, an intermediate treatment may be carried out between the reducing and neutralizing steps.

The following Examples illustrate the invention in greater detail.

EXAMPLE 1

| Permanent waving composition for natural hair | |
|---|---|
| Ammonium thioglycollate (60%) | 21.5(Gew.-%) |
| Ammonium hydrogencarbonate | 5.0 |
| Chlorophyllin, 6% | 0.1 |
| Solubilizer (polyoxyethylene derivate) | 0.8 |
| Urea | 1.0 |
| 1,2-Propanediol | 4.0 |
| Alkyl dimethyl polysiloxane/ polyethyloxazoline grafted copolymer (Organopolysiloxane A-1 of EP-A No. 640 643) | 0.4 |
| Cocoamidopropyl betaine | 1.0 |

| Permanent waving composition for natural hair | |
| --- | --- |
| Foam inhibitor, opacifier, dyestuff | q.s. |
| Water | @ 100.0 |
| Ammonia to adjust pH-value to | pH 8.5 |

The composition was applied onto the wound hair, left to act for 20 minutes at about 30° to 40° C., rinsed and then neutralized with a 3% hydrogen peroxide solution. Upon removal of the curlers and another neutralizing step, the hair was dried.

The hair showed uniform and expressive waves with a pleasant shine, soft touch and excellent combability.

An omission of the grafted copolymer led to a distinctly less homogeneous and expressive waving result showing reduced shine, a coarser touch and less combability.

EXAMPLE 2

| Neutral permanent waving composition | |
| --- | --- |
| Composition A: | |
| Ammonium hydrogencarbonate | 1.0(g) |
| Cationic polymer (Polyquaternium-2) | 0.5 |
| Nonionic solubilizer | 0.8 |
| Alkyl dimethyl polysiloxane/polyethyl oxazoline grafted copolymer (Organopolysiloxane A-2 of EP-A 640 643) | 0.1 |
| Cocamidopropyl betaine | 1.5 |
| Foam inhibitor, opacifier, perfume | q.s. |
| Water | @ 75.0 |
| Ammonia to adjust pH-value to | pH 9.4 |
| Composition B: | |
| Glycerol monothioglycollate, 75% | 25.0(g) |

Immediately before application, the two compositions were admixed and the mixture (pH 7.1) was applied onto the hair. Thereafter the hair was permed and neutralized as described in Example 1.

The permanent wave achieved was significantly more regularly shaped, it had a softer and more relaxed touch, more shine and improved combability than a test curl performed in a half-side test with a comparison solution containing no grafted copolymer.

EXAMPLE 3

| Permanent waving solution for natural hair | |
| --- | --- |
| Composition A: | |
| Ammonium hydrogencarbonate | 4.5(g) |
| Cationic polymer (Polyquaternium-4) | 1.0 |
| Nonionic solubilizer | 0.8 |
| 1,2-Propandiol | 1.0 |
| Organopolysiloxane/polyethyloxazoline grafted copolymer (Organopolysiloxane A-1 of EP-A 640 643) | 0.1 |
| Cocamidopropyl betaine | 1.0 |
| Foam inhibitor, opacifier, perfume | q.s. |
| Water | @ 75.0 |
| Ammonia to adjust pH-value to | pH 8.6 |

| Permanent waving solution for natural hair | |
| --- | --- |
| Composition B: | |
| Ammonium thioglycollate, 70% | 18.0(g) |
| Thiolactic acid | 1.0 |
| Cysteine.HCl | 2.0 |
| 1,2-Propanediol | 0.5 |
| Water | @ 28.0 |
| Ammonia to adjust pH-value to | pH 5.5 |

The two compositions were separately filled into a two-compartment can and mixed immediately before application.

The mixture obtained (pH 7.4) was applied onto the hair; thereafter the permanent waving and neutralizing processes were performed as described in Example 1.

A regularly shaped and expressive permanent waving result was achieved; the hair showed genuine luster, pleasant and soft touch with good combability.

EXAMPLE 4

| Permanent wave for dyed hair | |
| --- | --- |
| Composition A: | |
| Ammonium hydrogencarbonate | 3.5(g) |
| Cationic polymer (Polyquaternium-6) | 0.5 |
| Nonionic solubilizer | 0.8 |
| Ethoxydiglycol | 1.5 |
| $C_{12}$–$C_{14}$-Alkyl polyglucoside (P.D. = ~1.5) | 1.0 |
| Organopolysiloxane/polyethyloxazoline grafted copolymer (Organopolysiloxane A-3 of EP-A 640 643) | 1.0 |
| Perfume, opacifier, dyestuff | q.s. |
| Water | @ 72.0 |
| Ammonia to adjust pH to | pH 8.3 |
| Composition B: | |
| Ammonium thioglycollate, 70% | 13.0(g) |
| Thiolactic acid | 0.5 |
| Cysteine.HCl | 1.0 |
| Glycine | 0.5 |
| 1,2-Propanediol | 1.0 |
| Water | @ 28.0 |
| Ammonia to adjust pH-value to | pH 5.4 |

The compositions A and B were filled separately into a two-compartment can.

After admixture, immediately before the permanent waving process, a pH-value of 7.25 was obtained.

After the usual permanent waving and neutralizing processes, this product achieved an even better perming result than that of Example 3.

We claim:

1. Composition for permanent waving of human hair comprising a) at least one reducing organic thio compound and (or) an inorganic sulfite; and b) at least one optionally quaternized aminoalkyl dimethyl polysiloxane/polyethyloxazoline copolymer of the formula

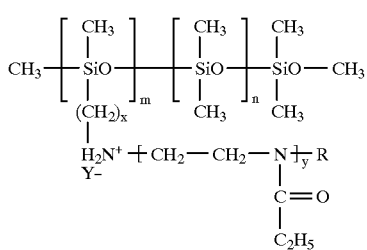

wherin m and n are whole numbers from 20 to 10,000, x is a number from 1 to 5 and y is a number from 5 to 30, R stands for a $C_1$–$C_{12}$-alkyl or aryl group and $Y^-$ is an anion.

2. Composition according to claim 1, comprising 0.05% to 5% by wt. of the optionally quaternized aminoalkyl dimethylpolysiloxane/polyethyloxazoline copolymer, calculated to the total composition.

3. Composition according to claim 2, comprising 0.1% to 2.5% by wt. of the optionally quaternized aminoalkyl dimethylpolysiloxane/polyethyloxazoline copolymer, calculated to the total composition.

4. Composition of claim 1, wherein m and n are whole numbers from 50 to 7000.

5. Composition of claim 1, wherein m and n are whole numbers from 100 to 50000.

6. Composition of claim 1, wherein x is 3.

7. Composition of claim 1, wherein R is chosen from the group consisting of a methyl, ethyl and benzyl group.

8. Composition according to claim 1, comprising 0.05% to 5% by wt. optionally quaternized aminoalkyl dimethylpolysiloxane/polyethyloxazoline copolymer, calculated to the total composition.

* * * * *